(12) United States Patent
Calais et al.

(10) Patent No.: US 6,677,373 B2
(45) Date of Patent: Jan. 13, 2004

(54) POLYMORPHIC B FORM OF 3-(CYCLOPROPYLMETHOXY)-4-[4-(METHYLSULFONYL)PHENYL]-5,5-DIMETHYL-5H-FURAN-2-ONE

(75) Inventors: Beatrice Calais, Meyzieu (FR); Evelyne Chassagneux, Millery (FR); Jean-Michel Bonard, Villeurbanne (FR)

(73) Assignee: Merial Limited, Harlow (GB)

( * ) Notice: Subject to any disclaimer, the term of this patent is extended or adjusted under 35 U.S.C. 154(b) by 0 days.

(21) Appl. No.: 10/117,854

(22) Filed: Apr. 8, 2002

(65) Prior Publication Data

US 2003/0050337 A1 Mar. 13, 2003

Related U.S. Application Data

(63) Continuation-in-part of application No. PCT/EP00/10421, filed on Oct. 9, 2000.

(30) Foreign Application Priority Data

Oct. 8, 1999 (EP) ................................. 99402482

(51) Int. Cl.$^7$ ................ A61K 31/34; C07D 305/12
(52) U.S. Cl. ........................... 514/473; 549/315
(58) Field of Search ..................... 549/315; 514/473

(56) References Cited

U.S. PATENT DOCUMENTS 5,474,995 A    12/1995    Ducharme et al. .......... 514/241

FOREIGN PATENT DOCUMENTS

| WO | 97/14691 | 4/1997 |
|---|---|---|
| WO | 97/16435 | 5/1997 |
| WO | 97/28121 | 8/1997 |
| WO | 98/41516 | 9/1998 |

*Primary Examiner*—Amelia Owens
(74) *Attorney, Agent, or Firm*—Frommer Lawrence & Haug LLP; William S. Frommer; Thomas J. Kowalski

(57) ABSTRACT

This invention is related to a polymorphic B Form of 3-(cyclopropylmethoxy)-4-[4-(methylsulfonyl)phenyl]-5,5-dimethyl-5H-furan-2-one characterized by the following parameters:

| cristalline system | Trigonal |
|---|---|
| space group | R-3 |
| description | hexagonal |
| unit-cell dimensions | |
| a (Å) | 18.183 |
| b (Å) | 18.183 |
| c (Å) | 26.950 |
| α (°) | 90 |
| β (°) | 90 |
| γ (°) | 120 |
| unit-cell volume (Å$^3$) | 7716.5 |
| number of molecules per unit-cell Z | 18 |
| Temperature of measurement (° K) | 293 |
| calculated specific gravity | 1.303 |
| weight absorption coefficient (cm$^{-1}$) | 2.11. |

12 Claims, 9 Drawing Sheets

US 6,677,373 B2

POLYMORPHIC B FORM OF 3-(CYCLOPROPYLMETHOXY)-4-[4-(METHYLSULFONYL)PHENYL]-5,5-DIMETHYL-5H-FURAN-2-ONE

RELATED APPLICATIONS

This application is a PCT continuation-in-part application of International Application Number PCT/EP00/10421 filed Oct. 9, 2000 and published as WO 01/27097 on Apr. 19, 2001, which claims priority from European Patent Application Number 99402482.6 filed Oct. 8, 1999.

Each of the applications and patents cited in this text, including each of the foregoing cited applications, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, various documents or references are cited in this text, either in a Reference List before the claims or in the text itself; and, each of the documents or references ("herein cited documents") and all of the documents cited in this text (also "herein cited documents"), as well as each document or reference cited in each of the herein cited documents (including any manufacturer's specifications, instructions, etc. for products mentioned herein and in any document incorporated herein by reference), is hereby expressly incorporated herein by reference. There is no admission that any of the various documents cited in this text are prior art as to the present invention. Any document having as an author or inventor person or persons named as an inventor herein is a document that is not by another as to the inventive entity herein. Also, teachings of herein cited documents and documents cited in herein cited documents and more generally in all documents incorporated herein by reference can be employed in the practice and utilities of the present invention.

SUMMARY OF THE INVENTION

The invention relates to a new crystalline form of 3-(cyclopropylmethoxy)-4-[4-(methylsulfonyl)phenyl]-5,5-dimethyl-5H-furan-2-one, herein designated as "Polymorphic Form B or Polymorph B", with pharmaceutically acceptable bases, which are inhibitors of cyclooxygenase-2 and useful as non-steroidal antiinflammatory drugs.

In another aspect, the invention relates to pharmaceutical compositions and methods of making and using the Polymorph B of 3-(cyclopropylmethoxy)-4-[4-(methylsulfonyl)phenyl]-5,5-dimethyl-5H-furan-2-one.

The invention also relates to a method for preparing polymorphic Form B comprising agitating polymorphic Form A in the presence of methanol.

The invention also relates to a method for preparing polymorphic Form B comprising agitating polymorphic Form A in the presence of polymorphic Form B seeds in methanol.

Non-steroidal antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase.

BACKGROUND OF THE INVENTION

Two forms of cyclooxygenase are known, corresponding to cyclooxygenase-1 (COX-1) or the constitutive enzyme, as originally identified in bovine seminal vesicles, and a second inducible form of cyclooxygenase, cyclooxygenase-2 (COX-2) which has been cloned, sequenced and characterized initially from chicken, murine and human and animal sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, it was concluded that the constitutive enzyme, COX-1, is responsible, in large part, for endogenous basal release of prostaglandins and hence is important in their physiological functions such as the maintenance of gastrointestinal integrity and renal blood flow. In contrast, it was concluded that the inducible form, COX-2 is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer and anti-angiogenic effects, but will have a diminished ability to induce some of the mechanism-based side effects. In particular, such a compound should have a reduced potential for gastrointestinal toxicity, a reduced potential for renal side effects and a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of premature labour, asthma and eosinophil related disorders. It will also be of use in the treatment of Alzheimer's disease, for decreasing bone loss particularly in postmenopausal women (i.e. treatment of osteoporosis) and for the treatment of glaucoma. It may also be useful for the treatment of age-related dementia, for decreasing osteoclastic bone loss and for treatment of glaucoma A brief description of the potential utility of cyclooxygenase-2 inhibitors is given in an article by John Vane, *Nature*, Vol. 367, pp. 215–216, 1994, and in an article in *Drug News and Perspectives*, Vol. 7, pp. 501–512, 1994.

Compounds having a potent COX-2 inhibitory effect are disclosed in WO 97/44027, WO 97/28121, WO 98/41516, WO 97/16435 and WO 97/14691.

WO 97/14691 discloses methylsulfonylphenyl-5H-furan-2-one compounds which are potent COX-2 inhibitors, namely 3-(cyclopropylmethoxy)-4-[4-(methylsulfonyl)phenyl]-5,5-dimethyl-5H-furan-2-one which was isolated in a crystalline form which is herein designated as "Polymorphic Form A or Polymorph A".

The formula of 3-(cyclopropylmethoxy)-4-[4-(methylsulfonyl)phenyl]-5,5-dimethyl-5H-furan-2-one is the following.

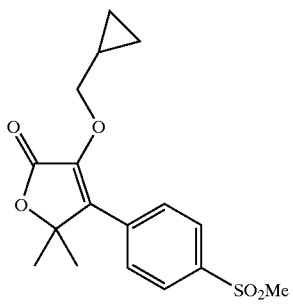

Recrystallization of polymorph A for purification purposes leaded to solubility problems in methyltertiobutylether.

Mixtures of 3-(cyclopropylmethoxy)-4-(4-methylsulfonyl)phenyl-5,5-dimethylfuranone solid at 6.3% weight in methyltertiobutylether could no longer be solubilised. After dilution and recrystallization, the powder obtained was analysed by X-Ray diffraction and showed a different pattern than the initial product.

The experiment was reproduced in several solvents such as methanol and dimethylformamide. The new solid form obtained was named polymorph B.

In a first embodiment the invention provides 3-(cyclopropylmethoxy)-4-[4-(methylsulfonyl)phenyl]-5,5-dimethyl-5H-furan-2-one in Polymorphic Form B, which is useful as a "non steroidal antiinflammatory agent" for the treatment of cyclooxygenase-2 mediated diseases.

Polymorph B possesses better flow characteristics than Polymorph A and is thermodynamically more stable than Polymorph A. Thus, Polymorph B is easier to handle (remove from vessel and transfer to filter), filter and dry than Polymorph A. Polymorph B is also easier to feed and micronize. Hence, the methods for its manufacture are more easily validated than that of Polymorph A.

Polymorph B may be characterized by the following parameters:

| Cristalline system | Trigonal |
|---|---|
| space group | R-3 |
| description | hexagonal |
| unit-cell dimensions | |
| a (Å) | 18.183 |
| b (Å) | 18.183 |
| c (Å) | 26.950 |
| α (°) | 90 |
| β (°) | 90 |
| γ (°) | 120 |
| unit-cell volume (Å$^3$) | 7716.5 |
| number of molecules per unit-cell Z | 18 |
| Temperature of measurement (° K) | 293 |
| calculated specific gravity | 1.303 |
| weight absorption coefficient (cm$^{-1}$) | 2.11 |

Polymorph B may be further be characterized by the following X-ray diffraction data calculated from crystalline structure.

TABLE 1

Powder X-Ray Diffraction Data calculated from crystalline structure

| d(Angs) | Intensity |
|---|---|
| 13.596 | w |
| 10.238 | w |
| 9.092 | s |
| 8.983 | m |
| 7.558 | vw |
| 6.798 | vw |
| 6.39 | m |
| 6.39 | vw |
| 6.194 | vw |
| 5.812 | m |
| 5.812 | w |
| 5.444 | w |
| 5.444 | vw |
| 5.249 | s |
| 5.119 | s |
| 5.1 | vw |
| 4.546 | vw |
| 4.532 | s |
| 4.532 | s |
| 4.492 | m |
| 4.461 | m |
| 4.448 | w |
| 4.311 | vw |
| 4.311 | vw |
| 4.155 | s |
| 4.155 | m |
| 4.056 | vw |
| 4.056 | vw |
| 4.027 | vw |
| 4.027 | vw |
| 3.995 | m |
| 3.995 | w |
| 3.895 | w |
| 3.74 | vw |
| 3.665 | vw |
| 3.665 | vw |
| 3.581 | m |
| 3.489 | vw |
| 3.489 | vw |
| 3.459 | vw |
| 3.436 | vw |
| 3.436 | vw |
| 3.413 | w |
| 3.413 | vw |
| 3.399 | vw |
| 3.393 | m |
| 3.393 | vw |
| 3.233 | vw |
| 3.209 | w |
| 3.209 | vw |
| 3.195 | w |
| 3.195 | vw |
| 3.184 | m |
| 3.184 | vw |
| 3.179 | vw |
| 3.128 | vw |
| 3.067 | vw |
| 3.031 | vw |
| 3.001 | vw |
| 3.001 | vw |
| 2.994 | vw |
| 2.958 | vw |
| 2.958 | vw |
| 2.932 | vw |
| 2.906 | vw |
| 2.906 | vw |
| 2.888 | vw |
| 2.853 | vw |
| 2.844 | vw |
| 2.813 | vw |
| 2.768 | vw |
| 2.753 | vw |
| 2.729 | vw |
| 2.729 | vw |

TABLE 1-continued

Powder X-Ray Diffraction Data calculated from crystalline structure

| d(Angs) | Intensity |
| --- | --- |
| 2.722 | vw |
| 2.722 | vw |
| 2.719 | vw |
| 2.667 | w |
| 2.667 | vw |
| 2.634 | vw |
| 2.624 | vw |
| 2.608 | vw |
| 2.522 | vw |
| 2.519 | vw |
| 2.519 | vw |
| 2.512 | vw |
| 2.504 | vw |
| 2.504 | vw |
| 2.501 | vw |
| 2.464 | vw |
| 2.464 | vw |
| 2.455 | vw |
| 2.438 | vw |
| 2.428 | vw |
| 2.428 | vw |
| 2.417 | vw |
| 2.364 | vw |
| 2.339 | vw |
| 2.301 | vw |

By way of comparison, the parameters and the X-ray diffraction data calculated from crystalline structure of polymorph A are reported hereunder:

TABLE 2

Powder X-Ray Diffraction Data for Single crystal Polymorph A

| d(A) | Intensity |
| --- | --- |
| 14.20 | M |
| 10.09 | S |
| 9.88 | S |
| 6.97 | Vw |
| 5.33 | M |
| 5.09 | W |
| 5.09 | Vw |
| 5.08 | M |
| 4.94 | M |
| 4.78 | W |
| 4.78 | M |
| 4.78 | M |
| 4.73 | M |
| 4.45 | M |
| 4.33 | M |
| 4.33 | M |
| 4.33 | M |
| 4.32 | M |
| 4.20 | Vw |
| 4.20 | W |
| 4.04 | W |
| 3.81 | W |
| 3.81 | Vw |
| 3.79 | Vw |
| 3.75 | W |
| 3.72 | m |
| 3.72 | m |
| 3.70 | w |
| 3.70 | w |
| 3.67 | w |
| 3.67 | w |
| 3.60 | w |
| 3.58 | w |
| 3.58 | w |
| 3.55 | w |

TABLE 2-continued

Powder X-Ray Diffraction Data for Single crystal Polymorph A

| d(A) | Intensity |
| --- | --- |
| 3.51 | w |
| 3.49 | vw |
| 3.39 | m |
| 3.39 | m |
| 3.32 | vw |
| 3.29 | w |
| 3.13 | vw |
| 3.11 | w |
| 2.94 | vw |
| 2.86 | vw |
| 2.86 | vw |
| 2.85 | w |
| 2.82 | vw |
| 2.63 | w |
| 2.31 | vw |

The powder X-ray diffraction pattern of polymorphs A and B is described hereafter in greater detail with respect to the enclosed figures.

BRIEF DESCRIPTION OF THE FIGURES

Figure 1:
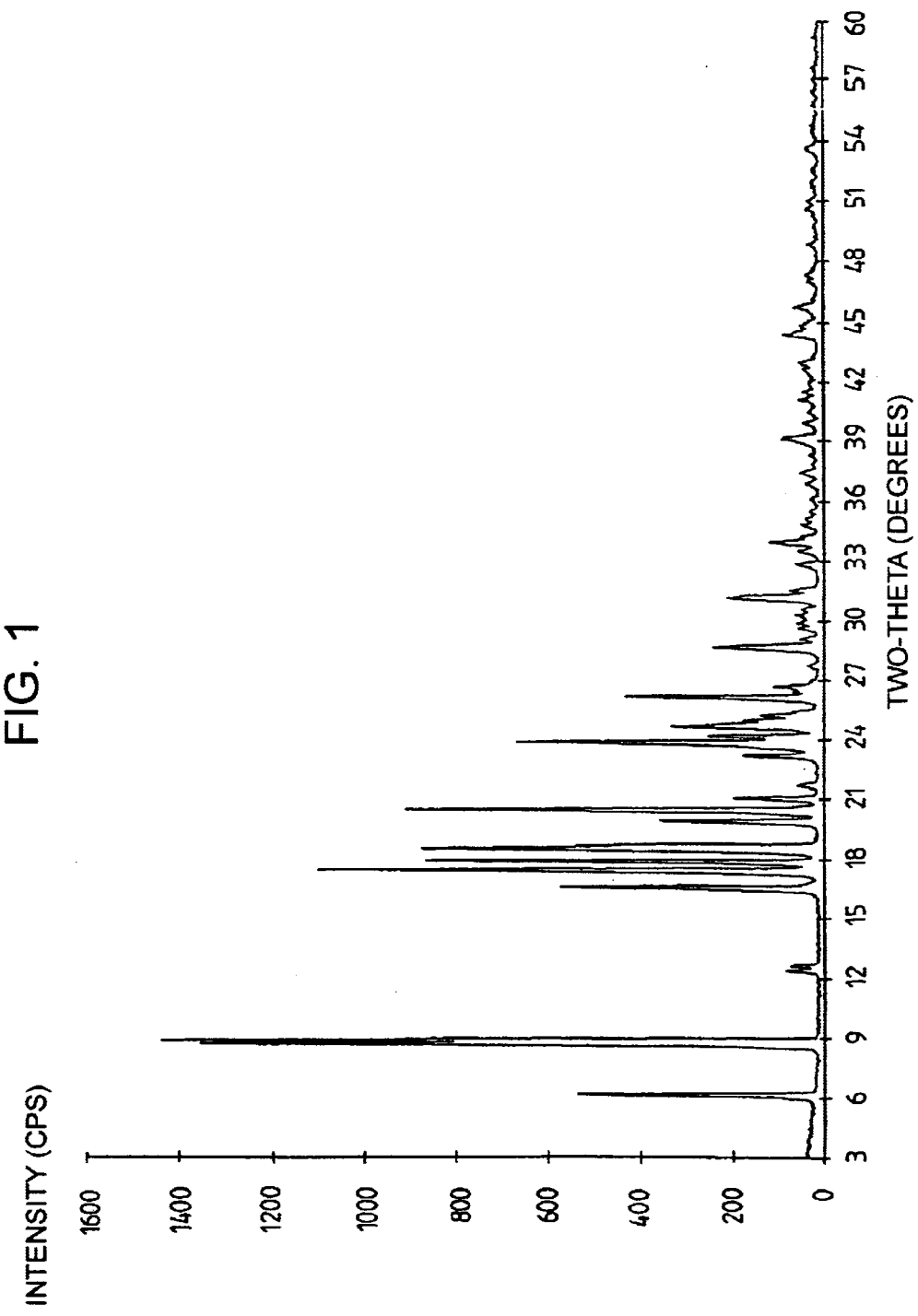
Figure 2:
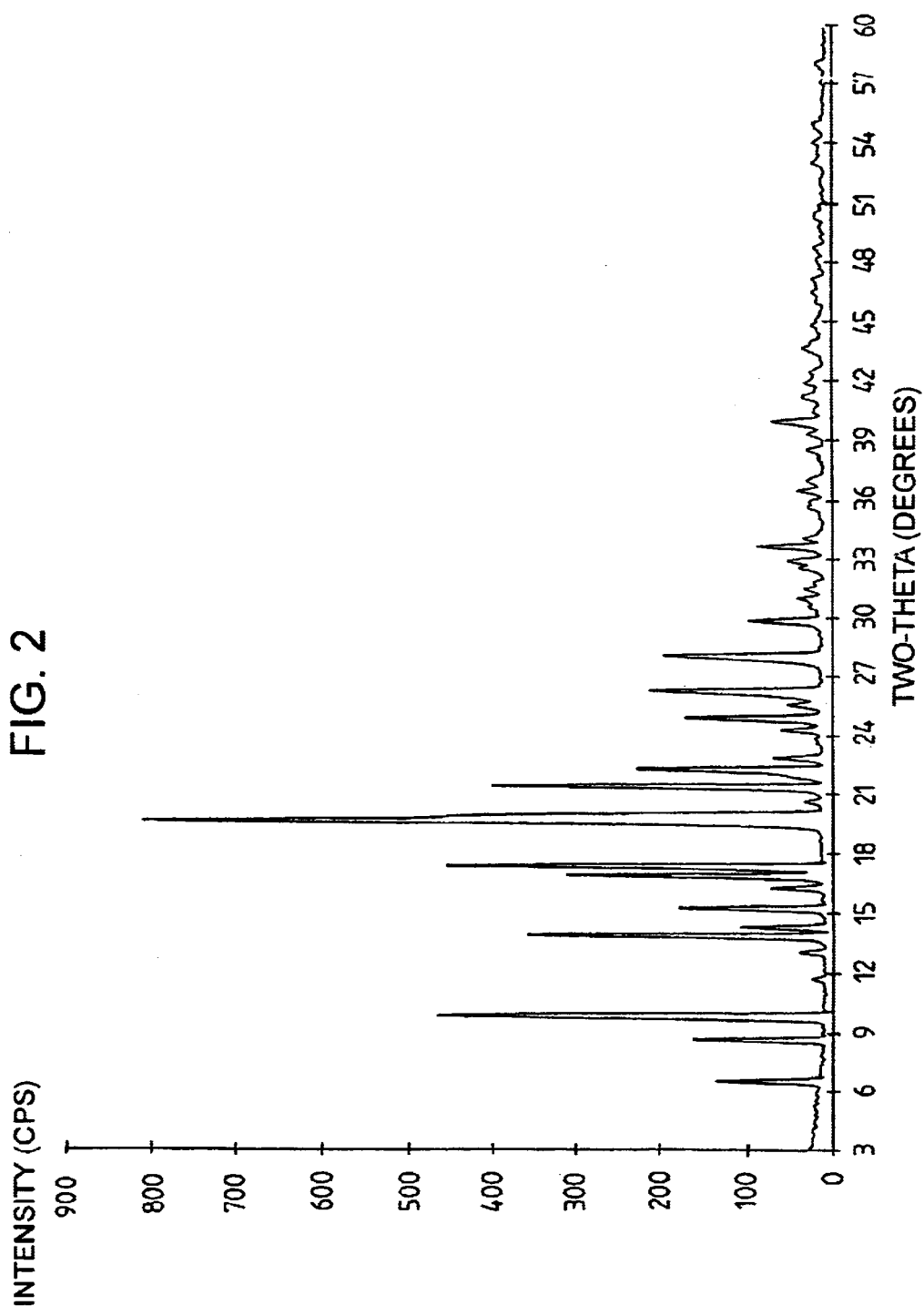
Figure 4:
Figure 3:
Figure 5:
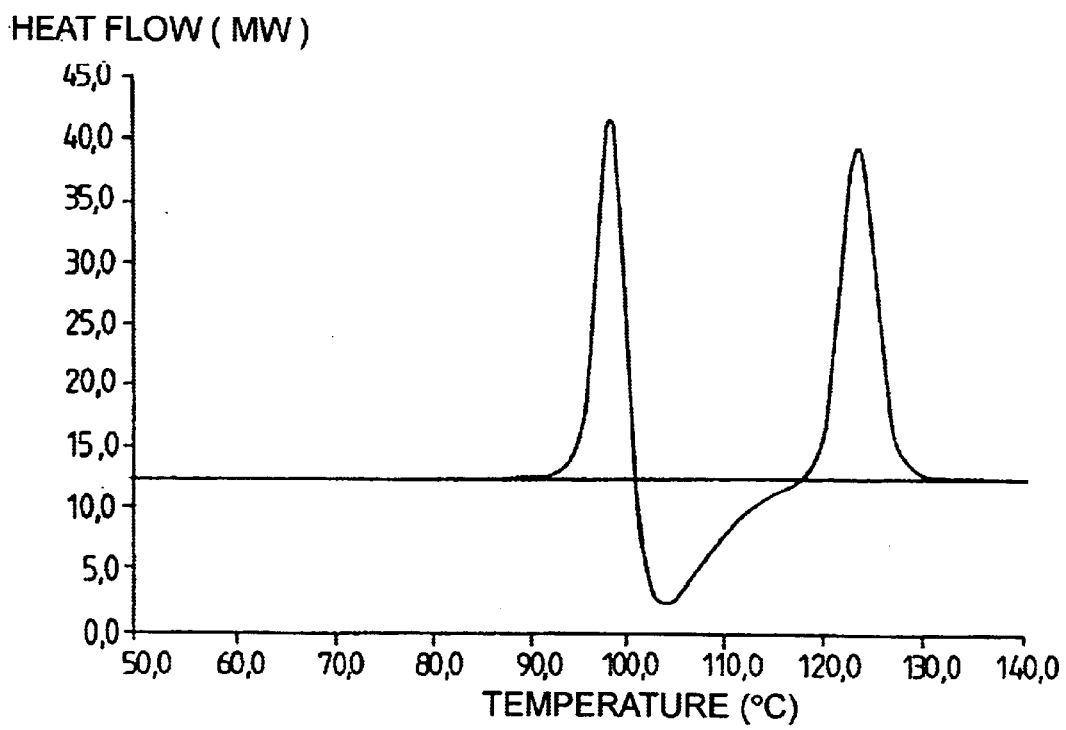
Figure 6:
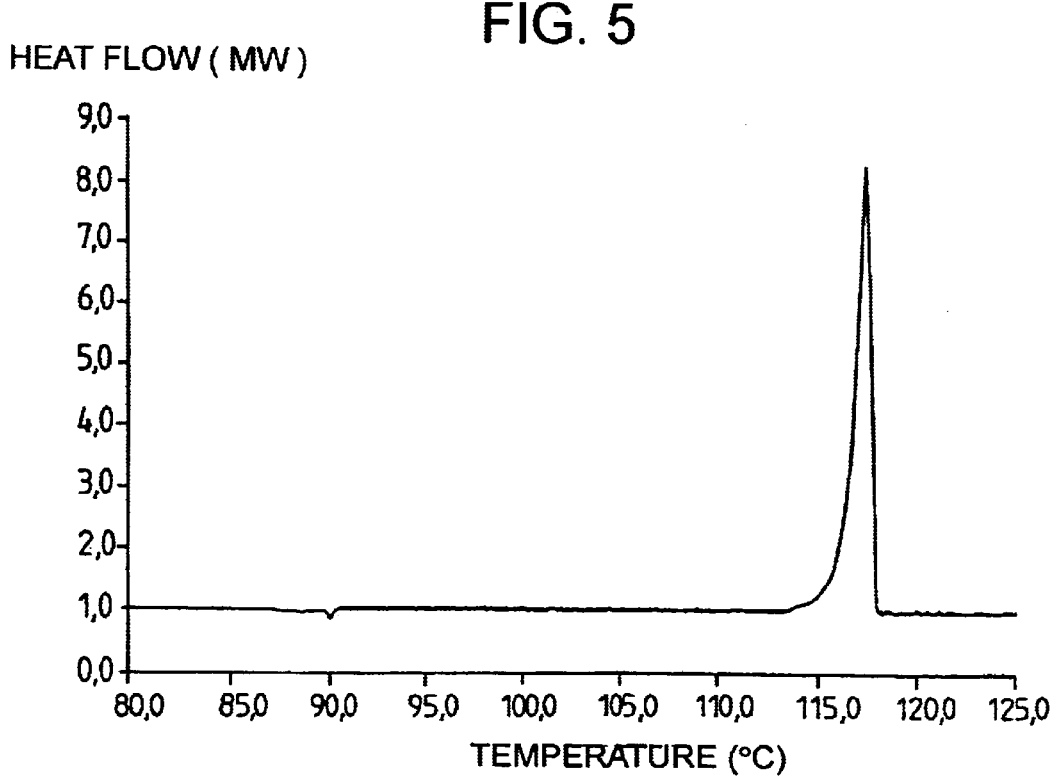
Figure 7:
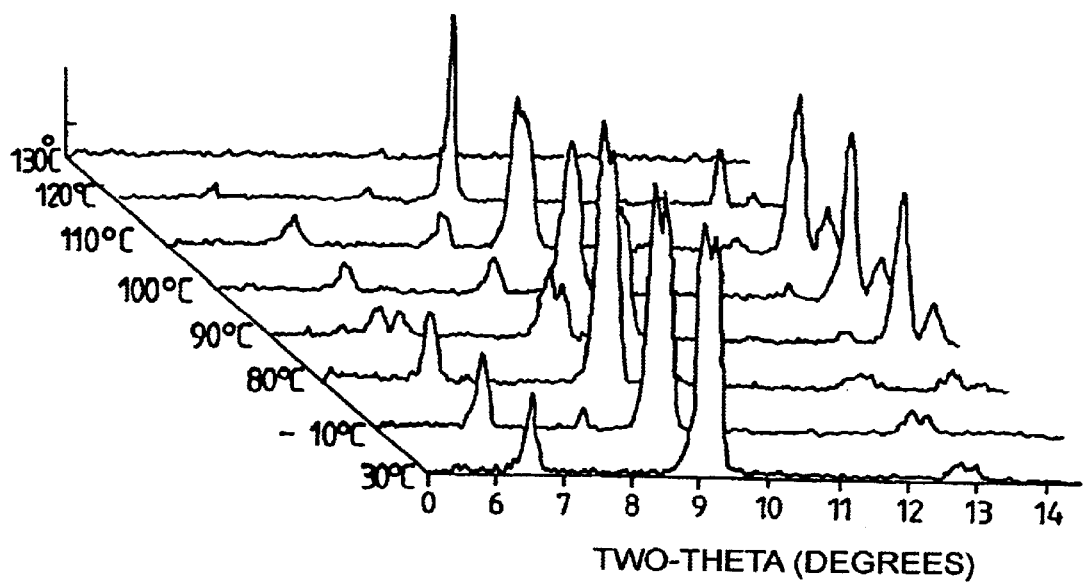
Figure 8:
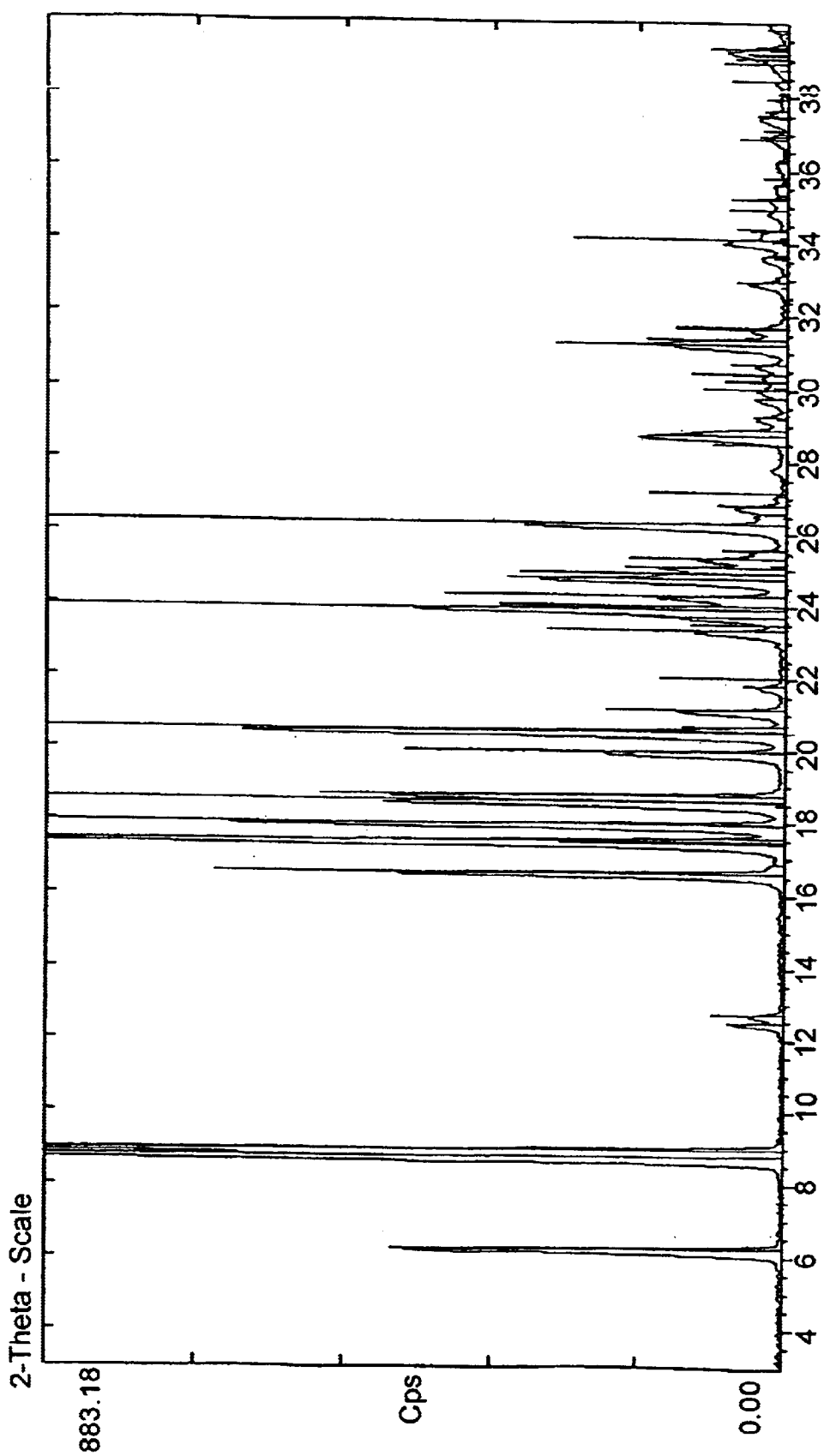

| | |
| --- | --- |
| FIG. 1 | shows the XRPD pattern of form A |
| FIG. 2 | shows the XRPD pattern of form B |
| FIG. 3 | shows the habit pattern of form A |
| FIG. 4 | shows the habit pattern of form B |
| FIG. 5 | is the DSC curve of a form A product heated at 40° C./mn |
| FIG. 6 | is the DSC curve of a form A product heated at 2° C./mn |
| FIG. 7 | shows the X-Ray diffraction patterns at 30° C., −10°, 80, 90, 100, 110, 120 and 130° C. with form A at 30° C. and form B appearing at 80° C. At 130° C., there is no signal as all the product is melted. |
| FIG. 8 | represents the X-ray diffraction pattern of the initial reaction medium used for converting Polymorph A to Polymorph B without seeding. |
| FIG. 9 | represents the X-ray diffraction pattern of the end reaction medium used for converting Polymorph A to Polymorph B. |
| FIG. 10 | represents the X-ray diffraction pattern of the initial reaction medium used for converting Polymorph A to Polymorph B with seeding. |
| FIG. 11 | represents the X-ray diffraction pattern of the end reaction medium used for converting Polymorph A to Polymorph B with seeding. |

DETAILED DESCRIPTION

Powder X-Ray Diffraction

The powder X-ray diffraction pattern of Polymorph A and Polymorph B was obtained by completely and uniformly filling the sample holder of the SIEMENS D5000 with the sample utilizing a spatula. The sample was then irradiated with the SIEMENS D5000 under the conditions described in Table I.

TABLE 1

Parameters for powder X-Ray Diffraction

| | |
| --- | --- |
| Instrument: | Siemens D5000 |
| X-Ray Target | Copper (d = 1.54 Å) |
| Voltage | 40 kV |
| Current | 30 mA |
| Detector | Scintillator |
| Two-theta range | 3°–60° |
| Scar Type | continuous |

TABLE 1-continued

Parameters for powder X-Ray Diffraction

| | |
|---|---|
| Chopper Increment | 0.01° |
| Beam Slit | 0.5° |
| Receiving beam scatter slit | 0.5° |
| Receiving detector slit | 6 mm |
| Atmosphere | Air |

The X-ray powder diffraction pattern of the micronized form of Polymorph A and B are represented respectively in FIGS. 1 and 2.

Handling Properties

It has been discovered that the new polymorphic form B has more advantageous handling properties in the micronization or preparation of pharmaceutical compositions.

After crystallization and before micronization, the Carr Index of B form is lower than 10 (in %). The Carr Index CI is defined as:

$$CI = \frac{P - L}{P}$$

where P is the packed bulk density (g cm$^{-3}$), L is the loose bulk density (g cm$^{-3}$). CI is also know as a compressibility index. A low figure for CI corresponds to a high degree of flowability.

The Carr Index way be calculated from Mercury Intrusion Porosimetry or measured by Tap—Tap.

Examples of Carr Index for unmilled products are given in table 2.

TABLE 2

| Polymorphic form | Crystallisation Process | Carr Index |
|---|---|---|
| A | Lab scale | 26 to 27 |
| A | Pilot scale | 29 to 33 |
| B | Recrystallisation in MTBE Lab scale | 2 to 3 |
| B | Recrystallisation in MTBE Pilot scale | 2 to 4 |

These better handling properties are due to:
bigger crystals (before micronization),
a more regular shape.

Form A is made of needle-like crystals (FIG. 3) when form B is mode of big faceted crystals (FIG. 4).

DSC (Differential Scanning Calorimetry)

When heated, form A transforms to form B depending on the heating rate.

For instance, when the heating rate is 40° C./mn, the DSC curve shows (FIG. 5):

an endothermal peak around 90–100° C. due to melting of A form, an exothermal peak corresponding to the transition A→B, an endothermal peak around 120° C. due to melting of B form, when the heating rate is 2° C./mn (FIG. 6) the DSC curve shows:

a very small exothermal peak corresponding to the transition A→B, an endothermal peak due to melting of B form.

Therefore, the transition A→B is under kinetic control as usual in case of polymorphism. The transition from A to B may also be followed by X-Ray under heating (FIG. 7).

According to Burger's rule ("On the Polymorphism of Pharmaceuticals an Other Molecular Crystals"—Theory of Thermodynamic Rules; A. BURGER—R; RAMBERGER—Mikrochimica Ada 1979; II, 259–271), the system is monotropic, and the B form is the most stable form.

In a second embodiment, the invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of Polymorph B.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of Polymorph B.

In a third embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a human or animal in need of such treatment of a non-toxic therapeutically effective amount of a compound of Formula I as disclosed herein.

The pharmaceutical compositions of the present invention comprise Polymorph B as an active ingredient, and may also contain a pharmaceutically acceptable carrier and optionally other therapeutic ingredients.

Polymorph B is useful for the relief of pain, fever and inflammation of a variety of conditions including signs associated with bacterial and viral infections, sprains and strains, tendonitis, myositis, neuralgia, synovitis, arthritis, including rheumatoid and osteoarthritis, ankylosing spondylitis, bursitis, colic gastroenteritis, colitis, cystitis, ophthalmitis, burns and injuries, and following surgical and dental procedures. In addition, such a compound may inhibit cellular neoplastic transformations and metastic tumor growth and hence can be used in the treatment of cancer. Polymorph B may also be of use in the treatment and/or prevention of cyclooxygenase-mediated proliferative disorders such as may occur in diabetic retinopathy and tumour angiogenesis.

Polymorph B will also inhibit prostanoid-induced smooth muscle contraction by preventing the synthesis of contractile prostanoids and hence may be of use in the treatment of premature labor, asthma and eosinophil related disorders. It will also be of use in the treatment of age-related dementia, and for the prevention of bone loss (treatment of osteoporosis) and for the treatment of glaucoma.

By virtue of its high cyclooxygenase-2 (COX-2) activity and/or its specificity for cyclooxygenase-2 over cyclooxygenase-1 (COX-1), Polymorph B will prove useful as an alternative to conventional non-steroidal antiinflammatory drugs (NSAID'S) particularly where such nonsteroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Polymorph B, will be useful as a partial or complete substitute for conventional NSAID'S in preparations wherein they are presently co-administered with other agents or ingredients.

Thus in further aspects, the invention encompasses pharmaceutical compositions for treating cyclooxygenase-2 mediated diseases as defined above comprising a non-toxic therapeutically effective amount of Polymorph B and one or more ingredients such as another pain reliever including acetominophen or phanacetin; a potentiator including acetominophen or phenacetin; a potentiator including caffeine; an $H_2$-antagonist, aluminum or magnesium hydroxide, simethicone, a decongestant including phenylephrine, phenylpropanolamine, pseudophedrine, oxymetalozine, ephinephrine, naphazoline, xylometazoline, propylhexedrine, or levodesoxyephedrine, an antiitussive including codeine, hydrocodone, caramiphen, carbetapentane, or dextramethorphan; a prostaglandin including misoprostol, enprostil, rioprostil, ornoprostol or rosaprostol; a diuretic; a sedating or non-sedating antihistamine.

In addition the invention encompasses a method of treating cyclooxygenase mediated diseases comprising: administration to a patient in need of such treatment a non-toxic therapeutically effective amount of Polymorph B, optionally co-administered with one or more of such ingredients as listed immediately above.

For the treatment of any of these cyclooxygenase mediated diseases Polymorph B may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily solutions, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets.

These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubrificating agents, for example, magnesium stearate, stearic acid or talc. the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredients is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinyl-pyrrolidone, gum tragacanth and gum acacia; dispersing or wetting agents may be a naturally-occuring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-aceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Polymorph B may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For oral or topical use, creams, ointments, gels, solutions, pastes, suspensions, etc., containing the compound of Formula I are employed. (For purposes of this application, topical application shall include mouth washes and gargles). Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of animals may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Examples for the preparation of Polymorph B are provided hereunder.

The synthesis of Polymorph A of 3-(cyclopropylmethoxy)-4-[4-(methylsulfonyl)phenyl]-5,5-dimethyl-5H-furan-2-one is disclosed in WO 97/14691 (Example 148).

EXAMPLE 1

Conversion of Polymorph A to Polymorph B by Stirring in Methanol Without Seeding To a 5 ml flask was added 1 g of methanol and 1.5 g of polymorph A.

Figure 9:
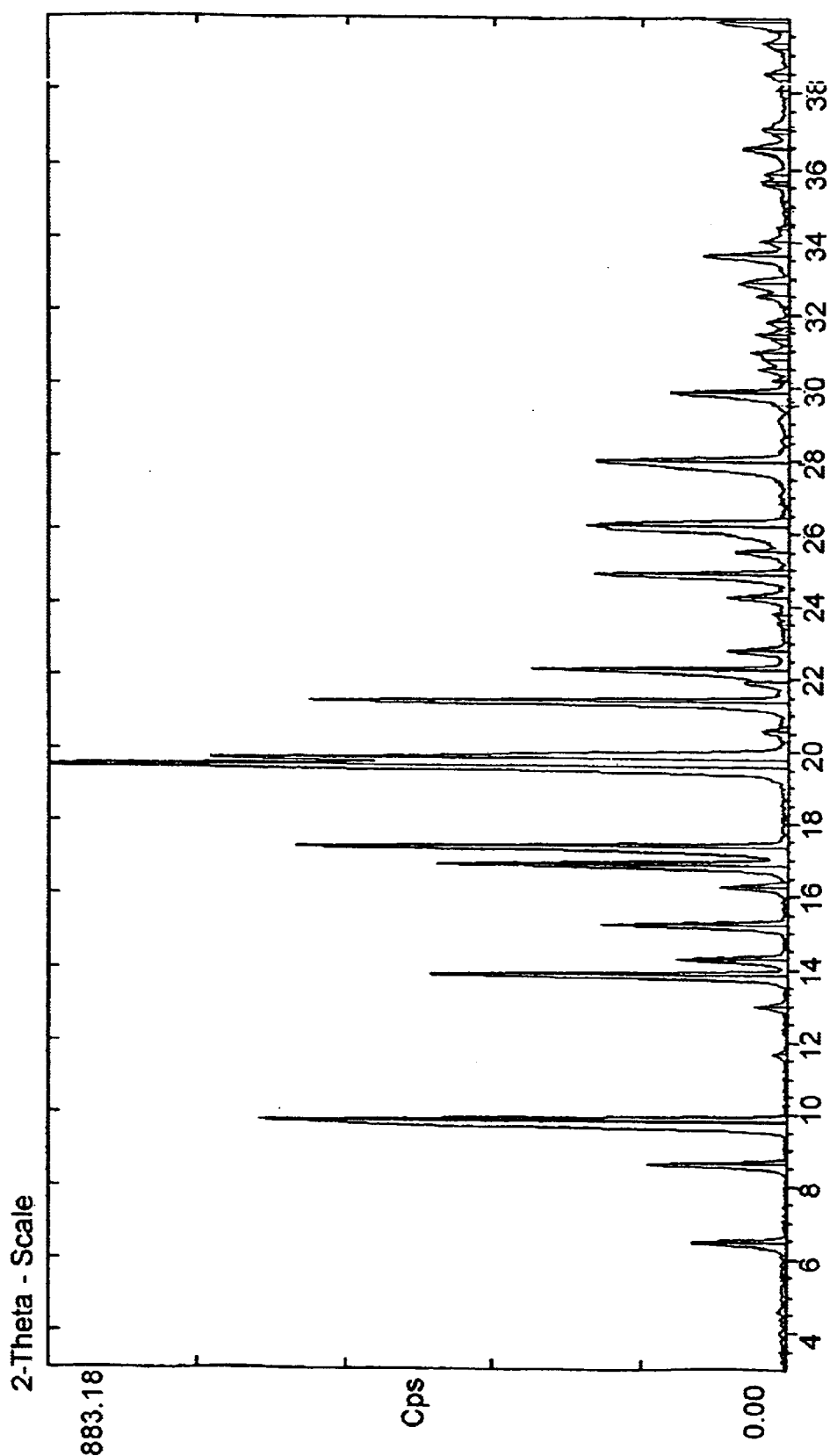

The agitation was maintained at room temperature for 50 minutes. All polymorph A had converted to polymorph B after this time. The results on the polymorphic form were confirmed by X-Ray diffraction (FIG. 9)

EXAMPLE 2

Conversion of Polymorph A to Polymorph B by Stirring in Methanol a 50/50 Mixture of the Two Solids.

Figure 10:
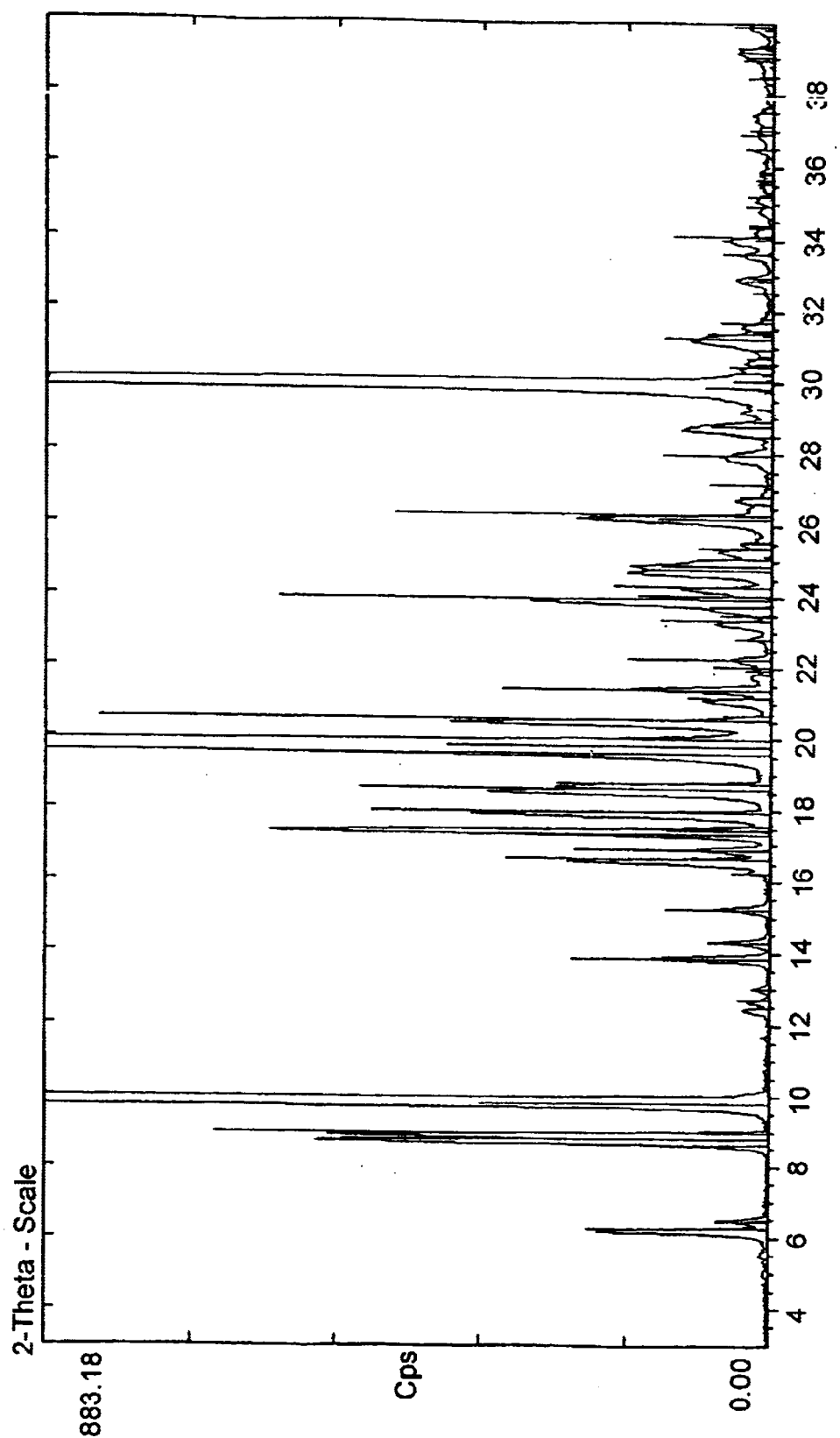
Figure 11:
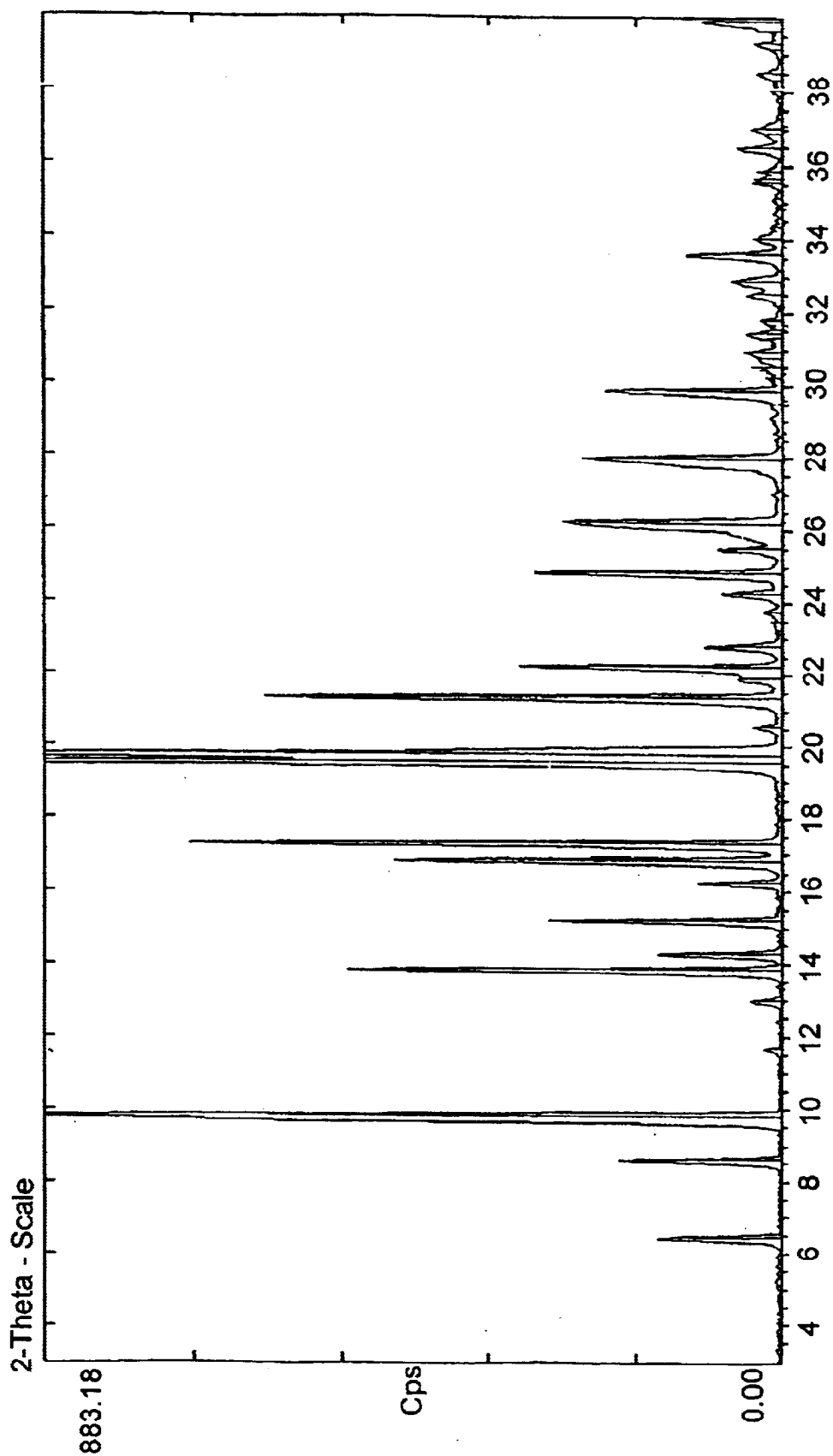

To a 5 ml flask was added 2.85 g of methanol, 0.95 g of polymorph A and 0.95 g of polymorph B The agitation was maintained at room temperature for 50 minutes. All polymorph A had converted to polymorph B after this time. The results on the polymorphic form were confirmed by X-Ray diffraction (FIGS. 10 and 11)

EXAMPLE 3

Recrystallization of Polymorph A to Polymorph B from a 30% Weight Solution in methylcyclohexan/tetrahyfrofuran (30/70 w/w) Seeded with Polymorph B.

To a 500 ml flask was added 154 g of polymorph A, 252 g of tetrahydrofuran and 108 g of methylcyclohexan. The mixture was heated at 60° C. The batch was in total solution at 58° C.

It was cooled to 48° C. over 10 min. and seeded with polymorph B. Immediate crystallization was observed. The batch was cooled at −13° C. over 30 min., filtered and dried at 70° C. under vacuum.

145.1 g of solid was isolated. The results on the polymorphic form were confirmed by X-Ray diffraction to be polymorph B.

EXAMPLE 4

Recrystallization of Polymorph A to Polymorph B by Precipitation Process in methylcyclohexan/tetrahyfrofuran (30/70 w/w) Seeded with Polymorph B.

To a 1 l flask was added 153 g of polymorph A and 179 g of tetrahydrofuran. The mixture was heated at 50° C. The batch was in total solution at 50° C. The solution is added to a 1 l flask containing 179 g of methylcyclohexan at 0° C. seeded with polymorph B in suspension. Immediate crystallization was observed. During the addition, medium is maintain at 0° C. and aged 60 min. after addition end. The batch is then filtered and dried at 70° C. under vacuum. 144.9 g of dried solid is obtained. The results on the polymorphic form were confirmed by IR analysis to be polymorph B

What is claimed is:

1. Polymorphic B Form of 3-(cyclopropylmethoxy)-4-[4-(methylsulfonyl)phenyl]-5,5-dimethyl-5H-furan-2-one characterized by the following parameters:

| | |
|---|---|
| cristalline system | Trigonal |
| space group | R-3 |
| description | hexagonal |

-continued

| unit-cell dimensions | |
|---|---|
| a (Å) | 18.183 |
| b (Å) | 18.183 |
| c (Å) | 26.950 |
| α (°) | 90 |
| β (°) | 90 |
| γ (°) | 120 |
| unit-cell volume (Å$^3$) | 7716.5 |
| number of molecules per unit-cell Z | 18 |
| Temperature of measurement (° K) | 293 |
| calculated specific gravity | 1.303 |
| weight absorption coefficient (cm$^{-1}$) | 2.11. |

2. Polymorphic B Form of 3-(cyclopropylmethoxy)-4-[4-(methylsulfonyl)phenyl]-5,5-dimethyl-5H-furan-2-one of claim 1, further characterized by the following X-ray diffraction data calculated from crystalline structure:

| d(Angs) | Intensity |
|---|---|
| 13.596 | w |
| 10.238 | w |
| 9.092 | s |
| 8.983 | m |
| 7.558 | vw |
| 6.798 | vw |
| 6.39 | m |
| 6.39 | vw |
| 6.194 | vw |
| 5.812 | m |
| 5.812 | w |
| 5.444 | w |
| 5.444 | vw |
| 5.249 | s |
| 5.119 | s |
| 5.1 | vw |
| 4.546 | vw |
| 4.532 | s |
| 4.532 | s |
| 4.492 | m |
| 4.461 | m |
| 4.448 | w |
| 4.311 | vw |
| 4.311 | vw |
| 4.155 | s |
| 4.155 | m |
| 4.056 | vw |
| 4.056 | vw |
| 4.027 | vw |
| 4.027 | vw |
| 3.995 | m |
| 3.995 | w |
| 3.895 | w |
| 3.74 | vw |
| 3.665 | vw |
| 3.665 | vw |
| 3.581 | m |
| 3.489 | vw |
| 3.489 | vw |
| 3.459 | vw |
| 3.436 | vw |
| 3.436 | vw |
| 3.413 | w |
| 3.413 | vw |
| 3.399 | vw |
| 3.393 | m |
| 3.393 | vw |
| 3.233 | vw |
| 3.209 | w |
| 3.209 | vw |
| 3.195 | w |
| 3.195 | vw |
| 3.184 | m |

-continued

| d(Angs) | Intensity |
|---|---|
| 3.184 | vw |
| 3.179 | vw |
| 3.128 | vw |
| 3.067 | vw |
| 3.031 | vw |
| 3.001 | vw |
| 3.001 | vw |
| 2.994 | vw |
| 2.958 | vw |
| 2.958 | vw |
| 2.932 | vw |
| 2.906 | vw |
| 2.906 | vw |
| 2.888 | vw |
| 2.853 | vw |
| 2.844 | vw |
| 2.813 | vw |
| 2.768 | vw |
| 2.753 | vw |
| 2.729 | vw |
| 2.729 | vw |
| 2.722 | vw |
| 2.722 | vw |
| 2.719 | vw |
| 2.667 | w |
| 2.667 | vw |
| 2.634 | vw |
| 2.624 | vw |
| 2.608 | vw |
| 2.522 | vw |
| 2.519 | vw |
| 2.519 | vw |
| 2.512 | vw |
| 2.504 | vw |
| 2.504 | vw |
| 2.501 | vw |
| 2.464 | vw |
| 2.464 | vw |
| 2.455 | vw |
| 2.438 | vw |
| 2.428 | vw |
| 2.428 | vw |
| 2.417 | vw |
| 2.364 | vw |
| 2.339 | vw |
| 2.301 | vw. |

3. A pharmaceutical composition comprising an amount which is effective for treating a COX-2 mediated disease of the Polymorphic B Form of 3-(cyclopropylmethoxy)-4-[4-(methylsulfonyl)phenyl]-5,5-dimethyl-5H-furan-2-one, according claim 1 together with a pharmaceutically acceptable base and an inert carrier material.

4. The pharmaceutical composition according to claim 3, wherein the effective amount is 5 to 1000 mg per day preferably 5 to 250 mg per day.

5. A process for preparing Polymorphic B Form 3-(cyclopropylmethoxy)-4-[4-(methylsulfonyl)phenyl]-5,5-dimethyl-5H-furan-2-one which comprises agitating Polymorphic A Form of 3-(cyclopropylmethoxy)-4-[4-(methylsulfonyl)phenyl]-5,5-dimethyl-5H-furan-2-one according to claim 1 with or without the presence of Polymorphic B seed in any solvent which shows a solubility for 3-(cyclopropylmethoxy)-4-[4-(methylsulfonyl)phenyl]-5,5-dimethyl-5H-furan-2-one and which does not react chemically with or bind to 3-(cyclopropylmethoxy)-4-[4-(methylsulfonyl)phenyl]-5,5-dimethyl-5H-furan-2-one.

6. The process for preparing Polymorphic B Form of 3-(cyclopropylmethoxy)-4-[4-(methylsulfonyl)phenyl]-5,5-dimethyl-5H-furan-2-one according to claim 5, wherein the solvent is selected from the group consisting of methanol, butyl ether, dimethylformamide or is selected from the group consisting of miscible combinations of dimethylformamide, methyl tertio butyl ether, and methanol.

7. The process for preparing Polymorphic B Form 3-(cyclopropylmethoxy)-4-[4-(methylsulfonyl)phenyl]-5,5-dimethyl-5H-furan-2-one according to claim 6, wherein the solvent is methanol.

8. The process of claim 5, wherein the Polymorph B seed is present in an amount of from about 0.5 to 1 percent by weight Polymorph A present.

9. Polymorphic B Form of 3-(cyclopropylmethoxy)-4-[4-(methylsulfonyl)phenyl]-5,5-dimethyl-5H-furan-2-one as defined in claim 1, prepared by the process which comprises agitating Polymorphic A Form of 3-(cyclopropylmethoxy)-4-[4-(methylsulfonyl)phenyl]-5,5-dimethyl-5H-furan-2-one with or without the presence of Polymorphic B seed in any solvent which shows a solubility for 3-(cyclopropylmethoxy)-4-[4-(methylsulfonyl)phenyl]-5,5-dimethyl-5H-furan-2-one and which does not react chemically with or bind to 3-(cyclopropylmethoxy)-4-[4-(methylsulfonyl)phenyl]-5,5-dimethyl-5H-furan-2-one.

10. A method for treating a COX-2 mediated disease which comprises administering to a host requiring such treatment an effective amount of Polymorphic B Form of 3-(cyclopropylmethoxy)-4-[4-(methylsulfonyl)phenyl]-5,5-dimethyl-5H-furan-2-one as defined in claim 1.

11. A method for treating a COX-2 mediated disease which comprises administering to a host requiring such treatment an effective amount of Polymorphic B Form of 3-(cyclopropylmethoxy)-4-[4-(methylsulfonyl)phenyl]-5,5-dimethyl-5H-furan-2-one as defined in claim 2.

12. A method for treating a COX-2 mediated disease which comprises administering to a host requiring such treatment an effective amount of Polymorphic B Form of 3-(cyclopropylmethoxy)-4-[4-methylsulfonyl)phenyl]-5,5-dimethyl-5H-furan-2-one as defined in claim 9.

* * * * *

UNITED STATES PATENT AND TRADEMARK OFFICE
CERTIFICATE OF CORRECTION

PATENT NO.   : 6,677,373 B2
DATED        : January 13, 2004
INVENTOR(S)  : Beatrice Calais et al.

It is certified that error appears in the above-identified patent and that said Letters Patent is hereby corrected as shown below:

<u>Title page,</u>
Item [73], Assignee, change "Merial Limited, Harlow (GB)" to -- MERIAL LIMITED, a company limited by shares registered in England and Wales (Registration Number 3332751) with a registered office at P.O. Box 327, Sandringham House, Sandringham Avenue, Harlow business Park, Harlow Essex CM19 5TG, England, and domesticated in Delaware, USA as MERIAL LLC, with a place of business at 3239 Satellite Blvd., Duluth, GA --

Item [30], Foreign Application Priority Data, change "99402482" to -- 99402482.6 --

Signed and Sealed this

Sixteenth Day of March, 2004

JON W. DUDAS
*Acting Director of the United States Patent and Trademark Office*